(12) United States Patent
Gargano et al.

(10) Patent No.: US 7,674,309 B2
(45) Date of Patent: Mar. 9, 2010

(54) HONEYCOMB FILTER DEFECT DETECTING METHOD AND APPARATUS

(75) Inventors: Patrick Michael Gargano, Addison, NY (US); Babak Robert Raj, Elmira, NY (US); William Paul Ryszytiwskyj, Corning, NY (US); John Charles Speeckaert, Painted Post, NY (US); David John Worthey, Elmira, NY (US)

(73) Assignee: Corning Incorporated, Corning, NY (US)

( * ) Notice: Subject to any disclaimer, the term of this patent is extended or adjusted under 35 U.S.C. 154(b) by 686 days.

(21) Appl. No.: 11/394,678

(22) Filed: Mar. 31, 2006

(65) Prior Publication Data
US 2007/0238191 A1 Oct. 11, 2007

(51) Int. Cl.
| B01D 39/06 | (2006.01) |
| B01D 46/00 | (2006.01) |
| G01D 21/00 | (2006.01) |
| G01N 21/00 | (2006.01) |
| G01J 3/46 | (2006.01) |
| G01M 3/04 | (2006.01) |

(52) U.S. Cl. ............... 55/523; 95/273; 356/237.1; 356/237.2; 356/237.3; 356/237.4; 356/237.5; 356/237.6; 356/337; 356/402; 73/40.7

(58) Field of Classification Search ............ 436/3, 436/5, 164, 177, 178, 181; 422/82.05, 101; 95/273; 55/97, 270, 523; 356/237.1–237.6, 356/337, 402; 73/40.7
See application file for complete search history.

(56) References Cited

U.S. PATENT DOCUMENTS

| 4,319,840 | A | 3/1982 | Kondo et al. | 356/241 |
| 5,102,434 | A | 4/1992 | Hijikata et al. | 55/97 |
| 5,411,682 | A * | 5/1995 | Nagashima | 264/36.15 |
| 5,640,236 | A | 6/1997 | Nagashima | 356/237 |
| 5,661,229 | A * | 8/1997 | Bohm et al. | 73/40.7 |
| 6,450,012 | B1 * | 9/2002 | Mayer et al. | 73/49.3 |
| 6,666,070 | B1 | 12/2003 | Hagg et al. | 73/38 |
| 7,012,678 | B2 | 3/2006 | Enomoto et al. | 356/237.1 |
| 7,283,224 | B1 | 10/2007 | Smithgall | 356/237.1 |

(Continued)

FOREIGN PATENT DOCUMENTS

EP 0 445 962 5/1996

(Continued)

OTHER PUBLICATIONS

U.S. Appl. No. 11/303,532, filed Dec. 16, 2005, Zoeller.

(Continued)

*Primary Examiner*—Walter D Griffin
*Assistant Examiner*—Amber Orlando
(74) *Attorney, Agent, or Firm*—Matthew B. McNutt

(57) ABSTRACT

A apparatus and method for detecting defects in a honeycomb body. In operation, the particulates emerge at an outlet end face of the honeycomb body through defects, if any, in the honeycomb walls and/or plugs and passes though a permeable member, such as a screen, where they are illuminated. The permeable member is disposed adjacent to and preferably in contact with the outlet end. Use of the permeable member improves the signal-to-noise ratio (SNR) such that defects may be more readily detected. The permeable member preferably includes an anti-reflective surface.

7 Claims, 6 Drawing Sheets

U.S. PATENT DOCUMENTS

| | | | |
|---|---|---|---|
| 7,290,439 B2 * | 11/2007 | Perkins et al. | 73/40.7 |
| 2003/0112437 A1 | 6/2003 | Enomoto et al. | 356/402 |
| 2004/0012776 A1 * | 1/2004 | Bae | 356/237.4 |

FOREIGN PATENT DOCUMENTS

| | | |
|---|---|---|
| JP | 02-191517 | 7/1990 |
| JP | 04-140409 | 5/1992 |
| JP | 07-136476 | 5/1995 |
| JP | 2000-065673 | 3/2000 |

OTHER PUBLICATIONS

U.S. Appl. No. 60/704,171, filed Jul. 29, 2005, Gargano et al.
U.S. Appl. No. 11/286,986, filed Nov. 22, 2005, Rae et al.

* cited by examiner

HONEYCOMB FILTER DEFECT DETECTING METHOD AND APPARATUS

FIELD OF THE INVENTION

The invention relates generally to apparatus and test methods for detecting defects in articles. More specifically, the invention relates to a method and apparatus for detecting defects in a honeycomb particulate filters.

BACKGROUND OF THE INVENTION

Wall-flow honeycomb filters are used to remove solid particulates from fluids, such as in exhaust gas streams. Prior Art FIG. 1 illustrates a typical prior art wall-flow honeycomb filter 100. The honeycomb filter 100 has an inlet end face 102 for receiving the inlet gas stream, an outlet end face 104 for expelling the outlet gas stream, and an array of generally parallel interconnecting porous walls 106 extending longitudinally from the inlet end face 102 to the outlet end face 104. The interconnecting porous walls 106 define a grid of inlet cell channels 108 and outlet cell channels 110. The outlet cell channels 110 are closed with porous plugs 112 where they adjoin the inlet end face 102 and open where they adjoin the outlet end face 104. Oppositely, the inlet cell channels 108 are closed with porous plugs (not shown) where they adjoin the outlet end face 104 and open where they adjoin the inlet end face 102. Such filters 100 are typically secured in a compliant mat and contained in a rigid housing (not shown). Fluid directed at the inlet end face 102 of the honeycomb filter 100 enters the inlet cell channels 108, flows through the interconnecting porous walls 106 and into the outlet cell channels 110, and exits the honeycomb filter 100 at the outlet end face 104.

In a typical cell structure, each inlet cell 108 is bordered on one or more sides by outlet cells 110, and vice versa. The inlet and outlet cells 108, 110 may have a square cross-section as shown in FIG. 1 or may have other cell geometry, e.g., circular, rectangle, triangle, hexagon, octagon, etc. Diesel particulate filters are typically made of ceramic materials, such as cordierite, aluminum titanate, mullite or silicon carbide. When particulates, such as soot found in exhaust gas, flow through the interconnecting porous walls 106 of the honeycomb filter 100, a portion of the particulates in the fluid flow stream is retained on or in the interconnecting porous walls 106. The efficiency of the honeycomb filter 100 is related to the effectiveness of the interconnecting porous walls 106 in filtering the particulates from the fluid. Filtration efficiencies in excess of 80% by weight of the particulates may be achieved with honeycomb filters. However, filtration efficiency or integrity of a honeycomb filter can be compromised by various defects, such as holes or cracks (such as fissures) and the like in the walls or plugs. Such defects allow the fluid to pass through the filter without proper filtration. Thus, in the manufacture of honeycomb filters, it may be desirable to test the honeycomb filters for the presence of such defects that may affect filtration efficiency or integrity. Honeycombs with detected defects may be repaired, or if irreparable, discarded.

One such method and apparatus for detecting defects is described in co-pending U.S. Provisional Application No. 60/704,171 filed Jul. 29, 2005 and entitled "Method And Apparatus For Detecting Defects In A Honeycomb Body Using A Particulate Fluid." This method of detecting defects involves generating a fog and directing it at an inlet end face of the filter, such that the fog enters the filter. Cells having defects in the walls or plugs readily allow the fog to flow into the adjacent cells or through the defective plugs. Thus, larger amounts of fog emerge at the outlet end face of the honeycomb filter from any such defective cell/plug as compared to other portions of the filter. A light source, such as a laser source, is positioned to emit a planar sheet of light slightly above the outlet end face of the filter to irradiate the fog emerging therefrom. An imaging camera is preferably installed above the filter to photograph the image generated by the light plane intersecting with the fog. Brighter spots correspond to cells/plugs containing defects. Once identified, cells/plugs corresponding with the spots may be repaired.

During testing, one problem that is encountered is that the background level of the fog exiting the filter can be so high as to obfuscate the images of the defective cells. This is particularly true when the filter is exposed to the fog for a long period of time, so as to become saturated. Thus, there is a need for a method and apparatus to further enhance the signal-to-noise ratio, such that defect in the filters may be more readily detected.

SUMMARY OF THE INVENTION

According to embodiments described herein, the invention is an apparatus for detecting defects in a honeycomb filter, for example in the plugs and/or walls thereof. The apparatus comprises a particulate source for providing particulates to an inlet face of the honeycomb filter, a permeable member, such as a screen, disposed adjacent to an outlet end face of the honeycomb filter, and a light source spaced from the member for illuminating particulates emerging through the permeable member. The permeable member improves the signal-to-noise ratio and also straightens the flow exiting from the end face, such that improved defect detection is enabled. The permeable member is preferably anti-reflective. This may be achieved by imparting a color to the member's surface; most preferably an anti-reflective black such as a flat or matte black. A fine mesh screen having a thread count of greater than 50 threads/inch has been found to be quite effective. The particulate source preferably generates fine particles suspended in a gas such as air. For example the particulates may be water particles suspended in a gas, i.e., a fog.

According to further embodiments, the invention is a method of detecting a defect in a honeycomb body, comprising the steps of providing a gas flow stream containing particulates to an inlet end face of the honeycomb body; flowing portions of the gas flow stream exiting an outlet end face of the honeycomb body through a permeable member, such as a screen, and illuminating any of the particulates exiting the permeable member with a light source. Thus, defective cells/plugs may be readily identified because locations of leaks/defects appear as bright spots. Preferably, the illuminated particles are also imaged, such as by a digital camera. This image is then compared to an image of the end face to determine which cells include defects. Preferably, the permeable member is moveable from a first location to a second location such that an image of the cell structure of the end face of the honeycomb may be obtained.

Advantageously, the permeable member allows the signal-to-noise ratio of the gas stream imaged to be enhanced, thereby making it easier to detect defects. In particular, the use of the permeable member enables the background reflection from the end face of the honeycomb to be decoupled. In addition, the use of the permeable member enables operating the apparatus at higher pressures, which improves throughput. The operating pressure may be above 30 Pa, for example.

Other features and advantages of the invention will be apparent from the following drawings, detailed description, and the appended claims.

DETAILED DESCRIPTION OF THE INVENTION

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings, discussions, and claims that follow.

Figure 1:
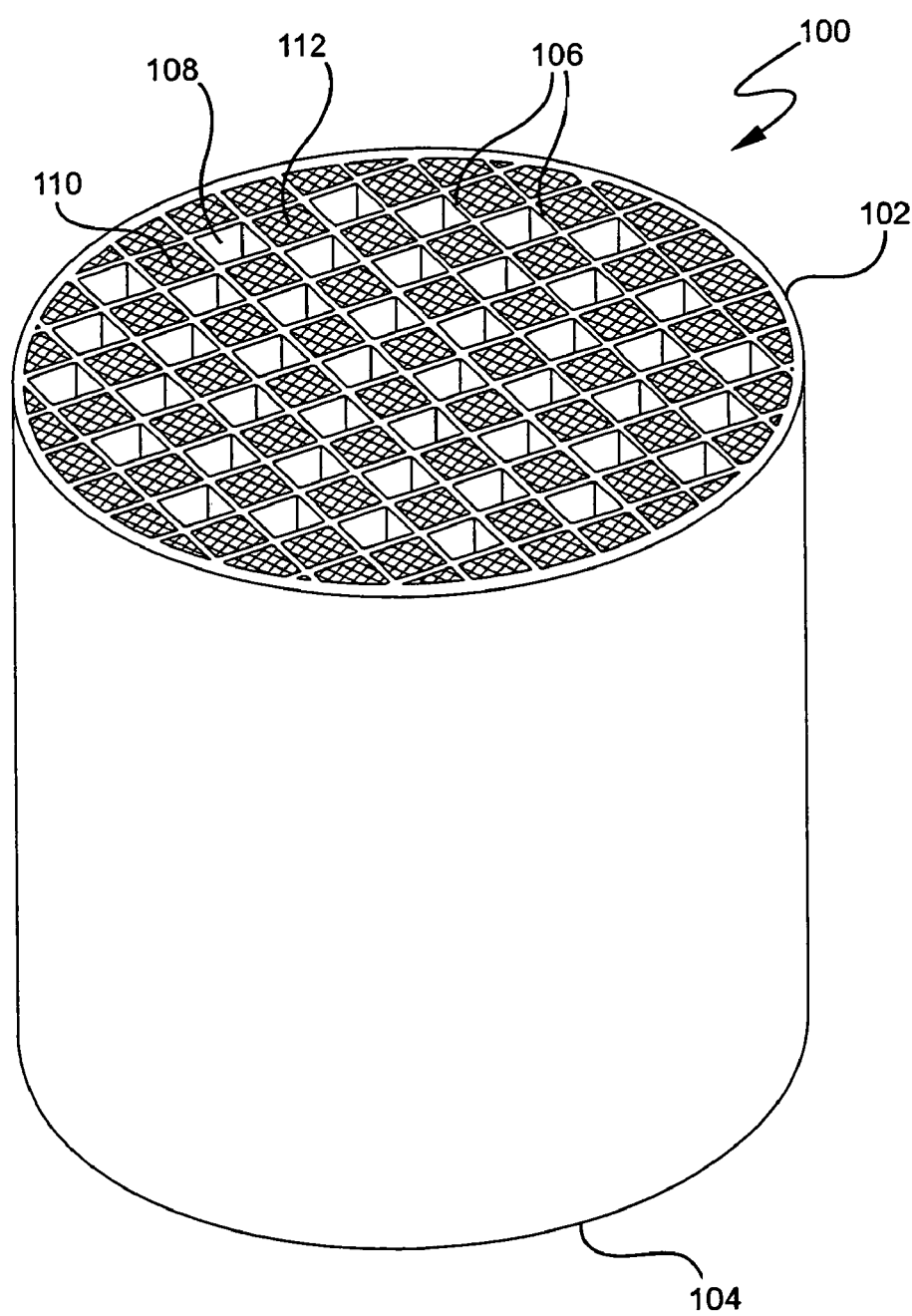
FIG. 1 shows an isometric view of a "Prior Art" honeycomb filter.
Figure 2:
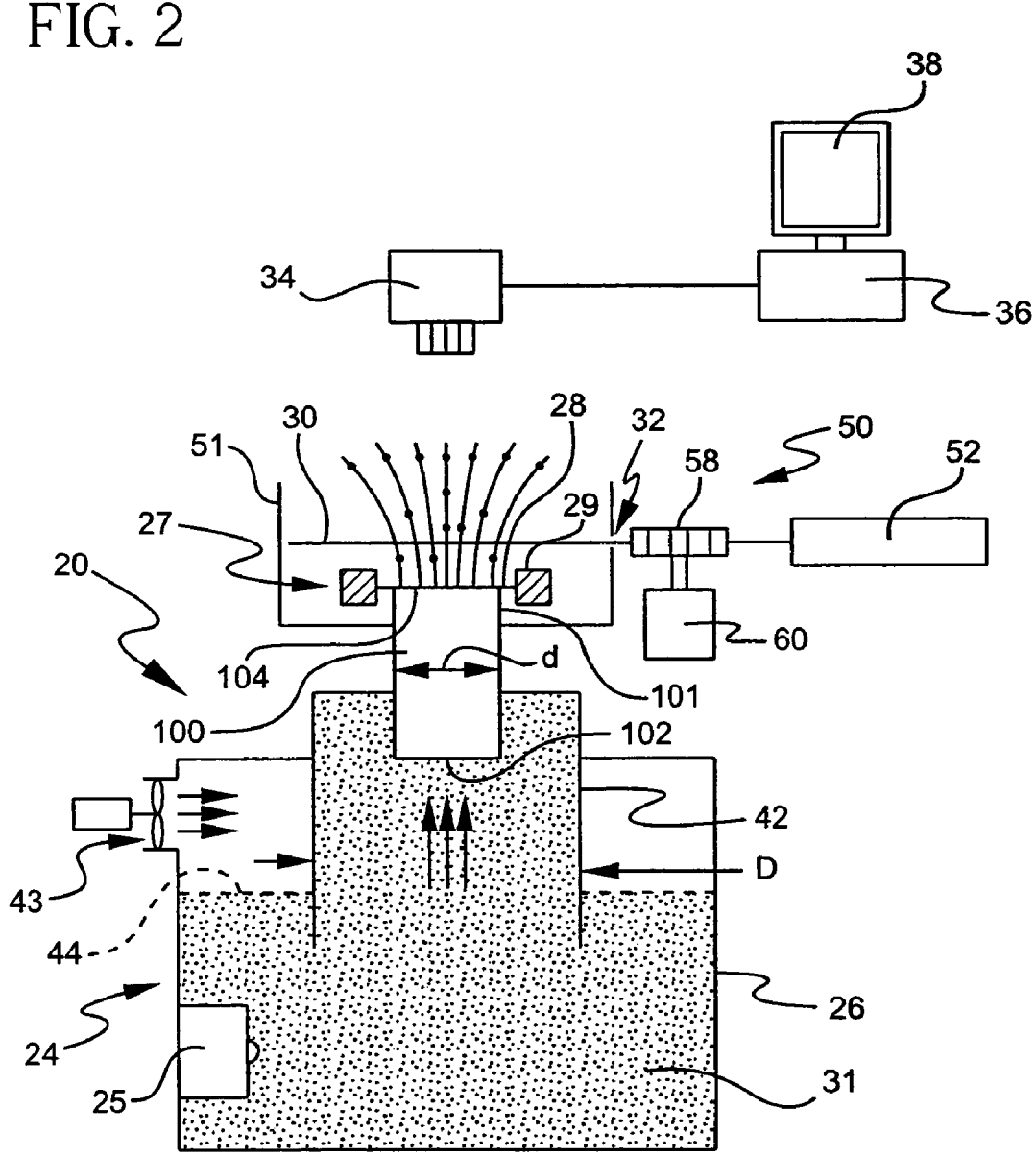
FIG. 2 shows a graphical front view of the apparatus for detecting defects in a honeycomb body according to embodiments of the invention.

The apparatus of the invention, as best illustrated in FIG. 2, provides a device 20 for detecting defects in a honeycomb body 100 having cells (channels) that are selectively end-plugged, such as in a wall flow filter or diesel particulate filter. The interior walls and/or plugs of the honeycomb body 100 may be porous. The porous walls and/or plugs are preferably tested for the presence of defects which may affect their performance. For example, the walls may include cracks (such as fissures) or holes which will allow unrestricted flow between adjacent cells thereby reducing filtration efficiency or affecting filter integrity. Additionally, the plugs may include defects such as partial fills, holes or cracks, or may even be missing or may be otherwise separated from the cell wall. The method and apparatus of the invention allows such defects to be readily detected.

The inspection testing device 20 of the invention includes a particulate source 24 which operates to supply a flow of gas (as indicated by arrows "22") which contains particulates suspended therein. The gas with suspended particulates is provided to an inlet end face 102 of the honeycomb body 100. The particulates suspended in the gas flow pass into the cell channels and through the porous walls and/or plugs of the body 100 and exit out through the outlet end face 104 thereof. Immediately upon exiting the end face 104, the gas containing particulates passes through a permeable member 28, such as a screen mounted adjacent to, and preferably engaged in direct contact with, the outlet end face 104. After exiting the permeable 28, the particulates in the flow are preferably illuminated by a plane of light 30 projected in the vicinity of the member; preferably parallel to the plane of the member and spaced a slight distance therefrom (preferably above). Defects in the plugs and/or walls may then be reliably detected in the honeycomb body 100 by inspection of the interference of the particulates and the plane of light 30.

In a preferred embodiment, an image indicative of the locations of defective cells is generated, for example by recording an image with a imager 34, such as a camera. The image corresponding to the defective cell locations may be stored in memory in a computer 36 and/or may also be displayed on a display 38. Defects in the wall and/or plugs show themselves as bright spots in the image above the honeycomb body 100, i.e., at the intersection with the plane 30. Accordingly, their location may be easily correlated with a cell defect location on the body 100. In particular, before laying the member 28 on top of the honeycomb 100, a previous image may be recorded of the end face 104, thereby capturing an image of the honeycomb cell structure, i.e., the location in coordinate space (along the plane of the end face 104) of the peripheral outline and the respective locations of the cells and plugs on the end face 104. This image may then be correlated with the other image illustrating the bright spots to assign various cells as including defects.

In operation, particulates, such as liquid particles, most preferably very fine liquid particles, are formed in a chamber 31 by a particle generator 25 of the particulate source 24. The particulates may be generated by nebulizing or atomizing or otherwise spraying through a small nozzle, a liquid. The liquid may be water-based or even glycol-based and, thus, is included in a fog. Water is most preferred. However, smoke or other fine suspended particulate matter could also be used and would benefit from the inventions herein. The particulates are preferably housed in a housing 26 and provided under pressure through a flow path, which is preferably defined by a pipe 42, between the particulate source 24 and the inlet end face 102 of the honeycomb body 100. The pipe 42 preferably includes a round cross-section (however, other cross-sectional shapes are possible, such as square, rectangular, etc.) and is preferably generally axially aligned with the honeycomb body 100. Further, preferably the inner dimension, D, (e.g., diameter) of the pipe 42 at the point where the particulate laden gas is provided to the first end face 102 (near the pipe's upper end) is larger than a maximum transverse outer dimension, d, of the honeycomb 100. This feature improves the uniformity of the flow velocity profile, by reducing the effect of boundary layer flow on the flow distribution of the gas, provided across the first end face 102. The provision of pressure, preferably at greater than 30 Pa (relative pressure between the inlet and ambient), is achieved by a fan 43 forcing air into the housing 26. In some embodiments, the pressure is between 30 and 70 Pa. A perforated partition 44 may be employed to minimize variations in pressure within the chamber 31.

Figure 3:
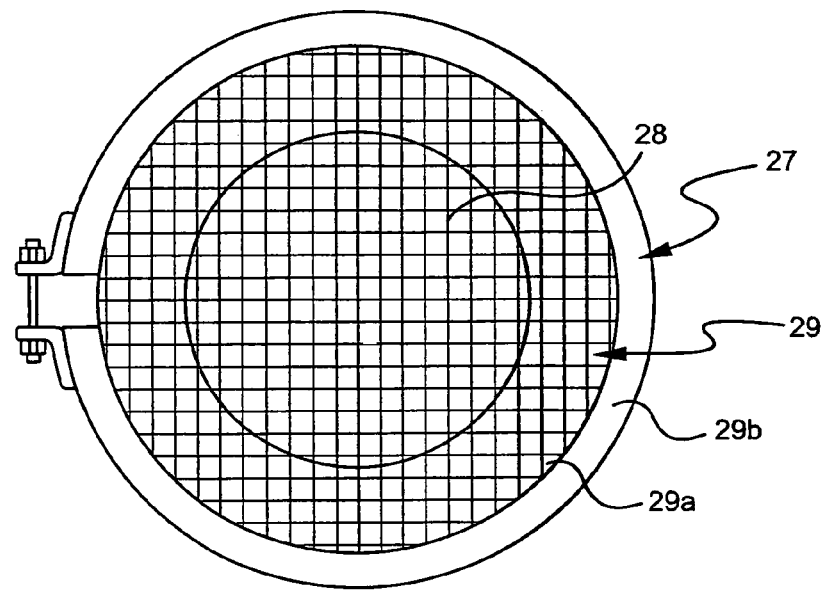
FIG. 3 is a top view showing the screen assembly of the apparatus according to embodiments of the invention.

Upon passing through the honeycomb body 100, the particulates contained in the gas flow pass through the permeable member 28. The permeable member 28 may be a screen, mesh, cloth, or perforated sheet, for example, which is preferably included in an assembly 27. The permeable member 28 is disposed adjacent to, preferably in contact with, the outlet end 104 of the honeycomb 100. The assembly 27, as best shown in FIGS. 2 and 3, includes a permeable member 28 mounted in a frame 29. The permeable member 28 is preferably manufactured from a filamentary material, such as a woven or interlaced strand or wire material having multiple oriented strands. The strands may be oriented in a generally perpendicular manner; although this orientation is not required. For example, the member may be woven in chain link orientation. Wire cloth or mesh was found to be particularly effective. Metal wire cloth, such as stainless steel wire cloth, may also be used. The permeable member 28 preferably includes a mesh density of greater than about 50 threads/inch, or even greater than 125 threads/inch, and in some embodiments greater than about 250 threads/inch. The diameter of the wire strands (filaments) in the mesh or cloth may be less than about 0.005 inch (less than about 127 µm), less than about 0.004 inch (less than about 102 µm), or even less than about 0.002 inch (less than about 51 µm). In one exemplary embodiment, the permeable member 28 includes wire mesh density of greater than about 50 threads/inch, and a diameter of the wire is preferably less than about 0.004 inch (less than about 102 µm). A fine screen having a 30 µm diameter and 325 threads/inch was found to work quite well. Permeable member 28 may also be chiffon or other knit cloth or mesh, or any other finely knitted, interlaced, or grid forming cloth material. The member 28 is preferably stretched across the frame 29 so as to construct a plane, and preferably held to the inner frame 29a by an adjustable outer frame 29b, such as the adjustable diameter ring shown.

Additionally, the member 28 may preferably include an anti-reflective surface. The anti-reflective surface is substantially absorbing of the light of the wavelength of the light source used for illumination. For example, the screen may be colored with a dark surface coloring, preferably flat black or matte black or other colors that are absorbing, such as brown or navy blue. Embodiments may include a coating, such as a black oxide coating. The dark coloring helps improve the signal-to-noise level between the signal and lower the background noise.

Figure 8:
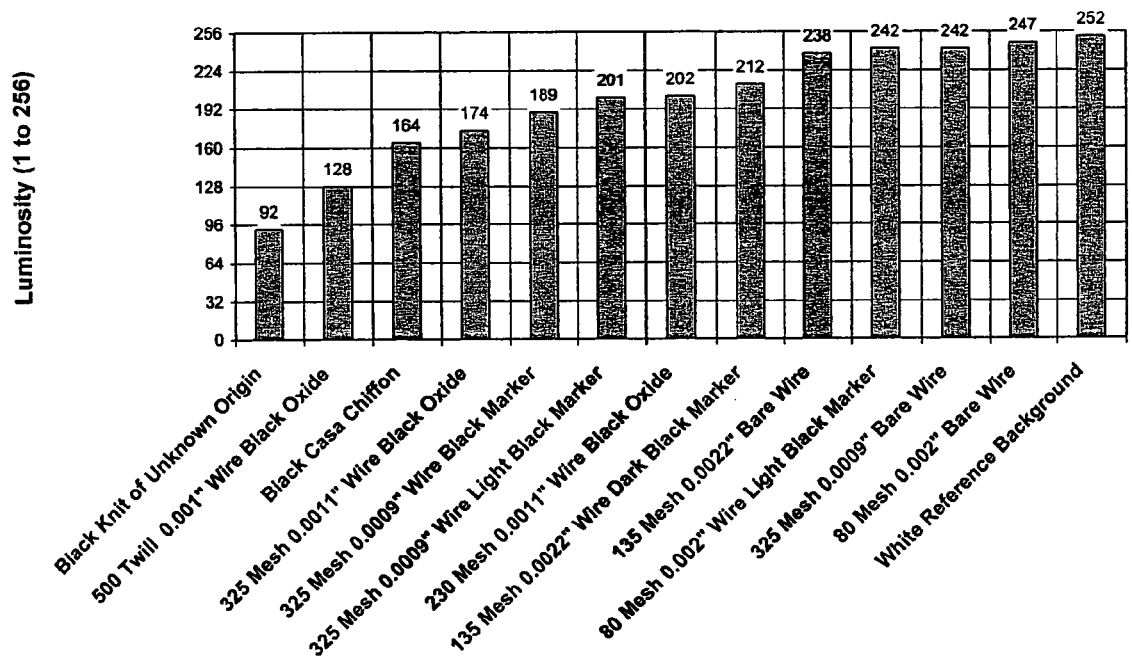
FIG. 8 is a plot showing luminosity versus permeable member type according to embodiments of the invention.

As best shown in FIG. 8, the luminosity versus type of permeable member is illustrated and surface color is indicated. It was discovered that good anti-reflective properties of the member are achieved when the surface exhibits a luminosity of less than 240 on a 1 to 256 scale utilizing a white light source; more preferably less than 215, or even of less than 180.

Stainless steel wire cloth coated with a black oxide coating was found to work well. Other types of permeable members which do not appreciably deflect the gas and particulate flow, thus to enable detection of defects may be used. It should be recognized that if the member 28 has a mesh thread density which is too coarse, the reflection from the end face 104 may not be appreciably reduced. Likewise, if the mesh density of the member 28 is too fine, flow will be impeded. Percent open areas in the member 28 of between about 30% and 80% are most desired.

In one embodiment, the illumination system 50 includes a light source 52 for generating a plane of light 30 adjacent to, and spaced slightly from, the outlet end face 104 of the honeycomb 100 and also spaced from the plane of the member 28. One example of a light source 52 is a laser, such as a red or green laser. The light source 52 preferably cooperates with optical elements, such as rotating faceted mirror 58, to convert the light beam to the planar sheet of light 30. Preferably, the mirror 58 is rotated, and includes, for example, 10 facets and produces a plane of light extending through an angle of about 72 degrees. The mirror 58 may be rotated by a motor 60 at greater than 500 rpm, for example. Thus, the illumination system 50 produces a plane of light 30, generally parallel to the end face 104 and a plane of the screen 28 which is large enough to fully span across the end face 104 of the honeycomb 100. The number of facets may be varied to extend or contract the angular range to accommodate varying size honeycomb bodies. Optionally, more than one light source may be used to form a uniform, preferably planar, sheet of light 30 across the outlet end face 104 of the honeycomb body 100. For example, U.S. Provisional Patent Application 60/638,201 filed on Dec. 21, 2004 by L. Zoeller, III and entitled "Method and System For Identifying Defective Cells In A Plugged Honeycomb Structure" describes rings of light sources to produce the plane of light. The light source 52 illuminates particulates emerging from the member 28.

Alternatively, it may be desirable to control the spread of the sheet of light 30. In which case, a slot 32 may be formed in the uprights 51 through which the light sheet 30 extends such that a well defined plane of light 30 is projected above the outlet end face 104. The width of the slot 32 on upright 51 is selected to control spread of the sheet of light 30. The uprights control eddy current and minimize air flow disturbances around the honeycomb 100. Preferably, the distance between the sheet of light 30 and the outlet end face 104 is such that the particulates emerging from the outlet end face 104 still have sufficient momentum to intersect the planar sheet of light 30. Thus, the sheet of light 30 should be as close as possible to the end face 104 and member 28 without interfering therewith. In one embodiment, the distance between the sheet of light 30 and the screen is in a range from 1/16 in. (1.6 mm) to ½ in. (12.7 mm). It should be recognized that other light sources may be used as well, provided a well defined plane of light is formed, for example a UV or IR laser.

After emerging from the member 28, the above-described illumination system 50 illuminates the particulates in the flow and an imager 34 is preferably used to capture an image of the X-Y position of particles illuminated (the bright spots) due to interference of a light plane 30 with the particulates emerging from the outlet end face 104 of the honeycomb body 100. The imager 34 records an image, preferably a digital image, of the interference pattern of the flow emerging from the member 28. The image is then processed to detect the presence of, and location of, defective cells/plugs, such that they may repaired. The processing includes comparing the image pixel-by-pixel against an intensity threshold. Above that pre-selected threshold, the presence of a defect is indicated. The imager 34, such as a camera or camcorder, is positioned above the outlet end face 104 of the honeycomb filter 100. The imager 34 captures an image of any illuminated particles flowing out of the face 104. In particular, the areas where defects are indicated show up as bright spots in the image. In the case of a single defect, the bright spot is a dot above the cell that has the increased particulate fluid flow (due to the defect). Thus, the location of the defect can be immediately identified (by the above processing step) for plugging. The imager 34 may further include an optical system, such as lenses, for focusing on the illuminated region. The imager 34 may include or be attached to an internal processor or computer 36 which processes information collected by the imager into image files and stores the image files in memory. The processor may support various types of image file formats, such as TIFF and JPEG. The computer system 36 may include a video monitor 38 and other peripheral devices necessary for interacting with the system, such as a keyboard and mouse (not shown). These peripheral devices are well known in the art and will not be discussed further. The image files from the imager 34 can be transferred to the processor 36 for further processing. The image files may also be displayed on the video monitor 38.

The imager 34 may be capable of detecting colors other than white light. For example, the imager 34 may be capable of detecting one or more colors selected from, for example, red, blue, and green. In the latter case, the sheet of light 30 may have a color that may be suitably detected by the imager, for example red. Since the sheet of light 30 is positioned above the outlet end face 104, particulates emerging at the outlet end face 104 would intersect the sheet of light 30, illuminating the particles at the locations where they intersect with the sheet of light 30.

Cells in the honeycomb body 100 having defects would discharge more particulates and larger particulates than cells not having defects. The size of the spots can provide an indication of the size of the defects in the honeycomb filter 100. If the image appears uniform, then there are no defects in the honeycomb filter 100. Advantageously, the use of the member 28 reduces the overall background level of the image thereby increasing the signal-to-noise ratio such that the bright spots associated with defects may be more readily detected. In other words, the threshold may be set lower. Further, more subtle defects may be detected.

To facilitate determining the location of the defective cells and size of the defects, such that any defects found may be located and repaired, it may be desirable to also image an outside peripheral profile 101 and the outlet end face 104 of the honeycomb body 100. The end profile image would show the location of cells, plugs and cell walls for the end of the honeycomb body 100 and its relationship to the outside peripheral profile 101. This end profile image is preferably obtained prior to installation of the screen 28 on the end of the honeycomb 100, or after its removal. Thus, the locations of the defects may be correlated to the respective cells in the honeycomb 100. It should also be recognized that the use of the screen 28 improves the overall correlation of the detected-to-actual location of defects by actually straightening the flow profile of the particulates exiting the outlet end face 104.

Figure 4:
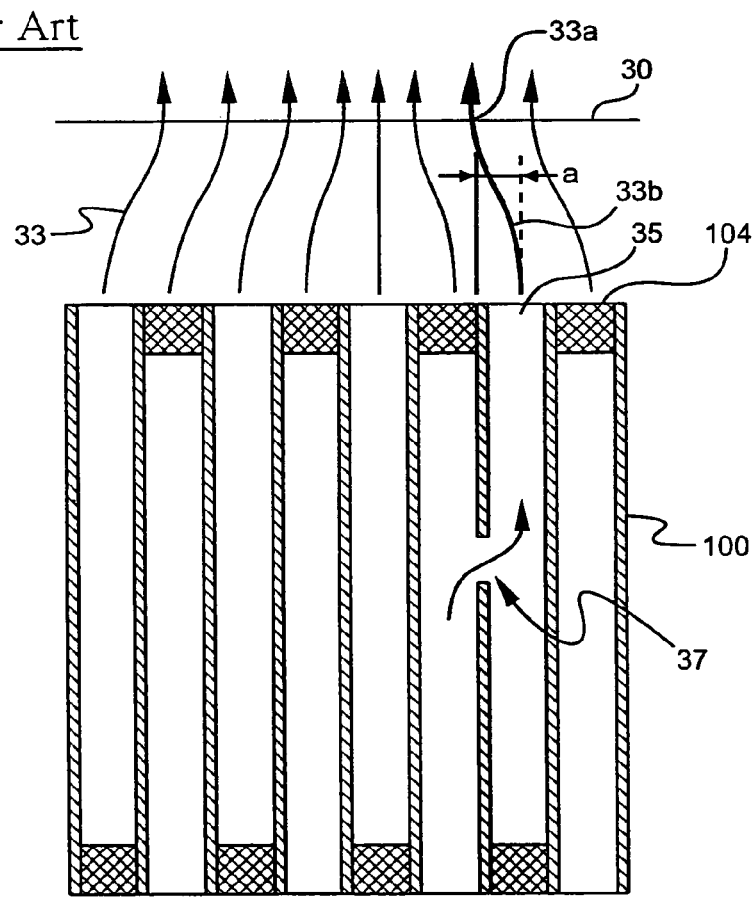
FIG. 4 is a cross sectional side view showing an apparatus according to the prior art.

As shown in FIG. 4, a flow profile of a prior art system is shown. As can be seen, during the inspection process, the flow lines (labeled 33) of the particulates in the flow exit the end face 104 and depart from a straight path. As such, at the location of the light plane 30, the indicated defective cell location 33a in the light plane 30, rather than being directly above the defective cell 35, may be slightly offset therefrom by a distance "a." Thus, to properly determine the location of the defective cell 35 due to a defect 37 in the honeycomb article 100, a correlation matrix is needed correlating the indicated defective cell location 33a to the actual defective cell location on the face 104. The larger flow of particulates from the defective cell 35 (indicated by thicker arrow) 33b is produced by flow passing through the low flow restriction of the wall defect 37 in the honeycomb 100.

Figure 5:
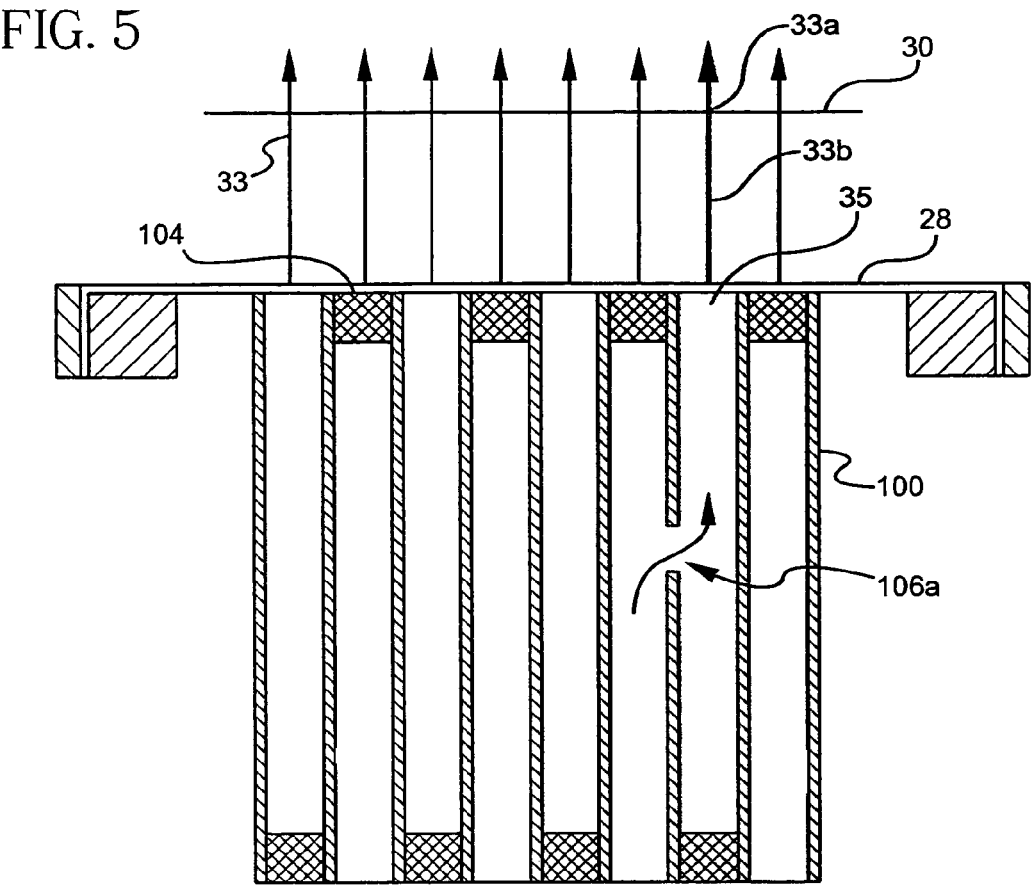
FIG. 5 is a cross sectional side view showing the apparatus according to embodiments of the invention.
Figure 6:
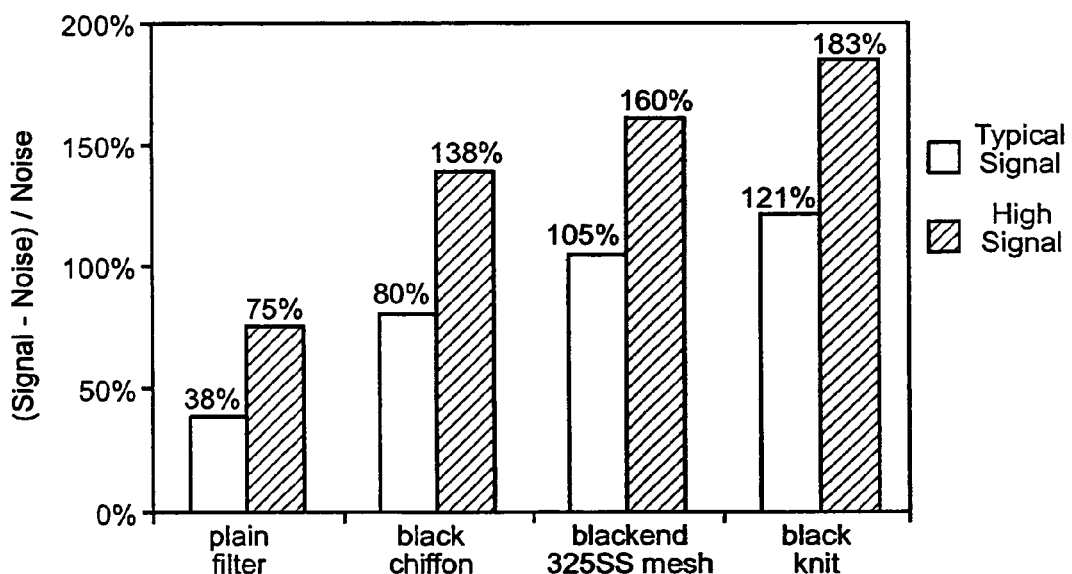
FIG. 6 shows a graph of the signal-to-noise ratio for various embodiments of the present invention as compared to the prior art.

Now referring to FIG. 5, the addition of the member 28 in contact with the end face 104 of the honeycomb 100 straightens the flow lines 33 and, in particular the higher relative flow 33b due to defect in wall 106a, such that the indicated defect location 33a in the light plane 30 is more nearly located above the actual cell defect location 35. Thus, it is easier to correlate the actual cell location 35 with the indicated location 33a. This affect is most pronounced at the peripheral cells. Accordingly, in addition to improving the image quality (by increasing the signal-to-noise ratio), the use of the member 28 also improves the ability to locate actual defective cell(s) and/or plugs. Thus, defects may be more accurately detected. In particular, the use of the member 28 reduces the overall background (noise) signal without appreciably reducing the signal from a defective cell. The member 28 does this by filtering out the component of reflection originating from the end face. Thus, the signal-to-noise ratio is improved is shown in FIG. 6 as compared to a plain filter test without the screen. In particular, the signal-to-noise ratio (SNR) is defined as:

SNR=(Signal−Noise)/Noise

The SNR may be increased by the present invention by a factor of 1.5 or more, or even 2.0 or more, as compared to an inspection method where the member is not used, as in the prior art. FIG. 6, for example, illustrates that the use of a black chiffon cloth increases the SNR to about 80%, or even over 100%. Similarly, SNR may be over 100% when using blackened mesh or black knit as the member 28. Other examples exhibited SNR of greater than 200%, or even greater than 300%. For example, a mesh with 325 threads/inch and 0.9 mil (about 23 μm) and open area of 49% which was colored black provided a SNR of 400%.

Figure 7:
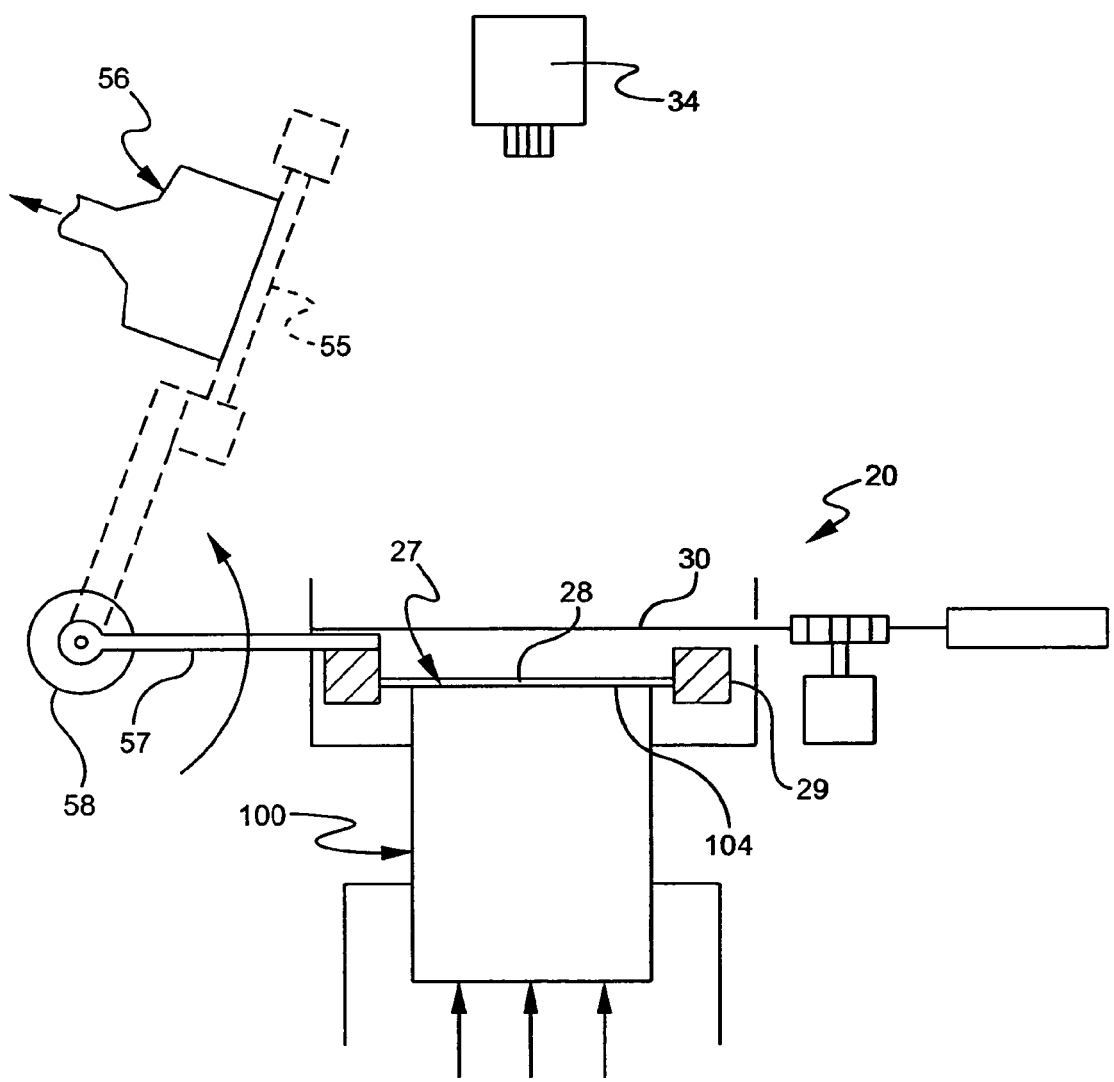
FIG. 7 is a partial side view showing an apparatus according to embodiments of the invention for removing and cleaning the screen after inspection testing.

In operation, as best shown in FIG. 7 illustrating the inspection apparatus 20, the assembly 27, including member 28 and frame 29, may be moved from a first location 55 (shown as dotted) to the location adjacent to, and preferably in contact with, the outlet end 104 of the honeycomb 100 by any suitable moving means. For example, the assembly 27 may be moved from the first location 55 by a motor 58 rotationally driving arm 57. As such, the screen assembly 27 may be moved out of the way such that the imager 34 may take an unobstructed image of the cell structure of the outlet end face 104 of the honeycomb 100; accordingly imaging the cell structure and locations relative to the periphery. This image is correlated, through a correlation matrix to the detected defects imaged from the interference of the particulates in the flow exiting the member 28 and the light plane 30. Thus, the defective cells may be detected, and the honeycomb body 100 may be moved offline and repaired, by a robot or the like. Additionally, when the member 28 is moved to the first location 55, the screen may be cleaned to remove any water and/or debris on the screen 28 by a cleaner 56. The cleaner 56 may be, for example, a vacuum head attached to a vacuum generator (not shown). Optionally, the member 28 may be otherwise cleaned, for example, by wiping with a wiper element, such as an elastomer wiper blade, blowing with compressed air or gas, or blotting with an absorbent member, such as a cloth or absorbent paper member. While the arm and member are positioned in the first position, the imager 34 may capture an image of the peripheral profile and cell structure (location of cell walls and plugs) such that the detected defects location at plane 30 may be correlated to the actual cell location on the end face 104 of the honeycomb 100.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method of detecting a defect in a honeycomb body, comprising the steps of:
   providing a gas flow stream containing particulates to an inlet end face of the honeycomb body;
   flowing portions of the gas flow stream exiting an outlet end face of the honeycomb body through a permeable member, wherein the permeable member includes an anti-reflective surface having a dark coloring, in order to improve the signal-to-noise ratio and also straighten the flow exiting from the end face, such that improved defect detection is enabled, and
   illuminating any of the particulates exiting the permeable member with a light source.

2. The method of detecting a defect of claim 1 wherein the step of illuminating further comprises providing a plane of light spaced from the permeable member.

3. The method of detecting a defect of claim 2 wherein the plane of light is generated by a laser.

4. The method of detecting a defect of claim 3 wherein the plane of light is generated by a reflecting the laser off from a rotating mirror.

5. The method of detecting a defect of claim 1 wherein the step of providing a gas flow stream containing particulates comprises generating a fog within a housing and supplying the fog to the inlet end face under pressure.

6. The method of detecting a defect of claim 5 wherein the pressure is greater than 30 Pa.

7. The method of detecting a defect of claim 1 wherein after the step of flowing portions of the gas flow stream exiting an outlet end face of the honeycomb body through the permeable member, a step of cleaning the permeable member is performed.

* * * * *